United States Patent [19]
Schiff et al.

[11] Patent Number: 5,865,795
[45] Date of Patent: Feb. 2, 1999

[54] SAFETY MECHANISM FOR INJECTION DEVICES

[75] Inventors: David Schiff, Highland Park, N.J.; Paul Mulhauser, New York, N.Y.

[73] Assignee: Medi-Ject Corporation, Minneapolis, Minn.

[21] Appl. No.: 609,137

[22] Filed: Feb. 29, 1996

[51] Int. Cl.$^6$ .................................................... A61M 5/30
[52] U.S. Cl. .................. 604/70; 604/72; 604/68
[58] Field of Search .................. 604/70, 72, 68, 604/69

[56] References Cited

U.S. PATENT DOCUMENTS

| | | |
|---|---|---|
| D. 304,616 | 11/1989 | Dunlap et al. . |
| D. 349,958 | 8/1994 | Hollis et al. . |
| 396,107 | 1/1889 | Nickerson . |
| 489,757 | 1/1893 | Reilly . |
| 1,567,517 | 12/1925 | Kisbey . |
| 1,973,706 | 9/1934 | Hawley . |
| 2,322,244 | 6/1943 | Lockhart . |
| 2,322,245 | 6/1943 | Lockhart . |
| 2,380,534 | 7/1945 | Lockhart . |
| 2,390,246 | 12/1945 | Folkman . |
| 2,398,544 | 4/1946 | Lockhart . |
| 2,413,303 | 12/1946 | Folkman . |
| 2,450,527 | 10/1948 | Smith et al. ............................ 285/177 |
| 2,459,875 | 1/1949 | Folkman . |
| 2,547,099 | 4/1951 | Smoot . |
| 2,605,763 | 8/1952 | Smoot . |
| 2,635,602 | 4/1953 | Hein . |
| 2,653,602 | 9/1953 | Smoot . |
| 2,670,121 | 2/1954 | Scherer et al. . |
| 2,671,347 | 3/1954 | Scherer . |
| 2,681,653 | 6/1954 | Kuhne . |
| 2,688,968 | 9/1954 | Scherer . |
| 2,699,166 | 1/1955 | Dickinson, Jr. et al. . |
| 2,704,542 | 3/1955 | Scherer . |
| 2,704,543 | 3/1955 | Scherer . |
| 2,705,953 | 4/1955 | Potez . |
| 2,714,887 | 8/1955 | Venditty . |
| 2,717,597 | 9/1955 | Hein, Jr. . |
| 2,722,931 | 11/1955 | May . |
| 2,737,946 | 3/1956 | Hein, Jr. . |
| 2,754,818 | 7/1956 | Scherer . |
| 2,762,369 | 9/1956 | Venditty . |
| 2,762,370 | 9/1956 | Venditty . |
| 2,764,977 | 10/1956 | Ferguson . |
| 2,789,839 | 4/1957 | Siebert . |
| 2,798,485 | 7/1957 | Hein, Jr. . |
| 2,798,486 | 7/1957 | Hein, Jr. . |

(List continued on next page.)

FOREIGN PATENT DOCUMENTS

| | | |
|---|---|---|
| 2028870 | 5/1991 | Canada . |
| 2071115 | 12/1992 | Canada . |
| 0 157 906 | 10/1985 | European Pat. Off. . |
| 0 460 961 | 6/1991 | European Pat. Off. . |
| WO 93/03779 | 3/1993 | European Pat. Off. . |
| WO 95/03844 | 2/1995 | European Pat. Off. . |
| WO 96/21482 | 7/1996 | European Pat. Off. . |
| 76202162 | 5/1986 | Taiwan . |
| 959397 | 6/1964 | United Kingdom . |
| 2249159 | 1/1994 | United Kingdom . |

Primary Examiner—Michael Bulz
Assistant Examiner—Tina T.D. Pham
Attorney, Agent, or Firm—Pennie & Edmonds LLP

[57] ABSTRACT

A safety mechanism for aiding in the prevention of accidental or unintentional discharge of a needleless injection device having a power unit, a housing, a plunger disposed within the housing, a trigger assembly, and a nozzle. The safety mechanism includes a locking member which is disposed at least partially on the exterior of the housing. The locking member works in concert with the triggering assembly to the prevent movement thereof, thereby preventing activation of the power unit to eject fluids through the nozzle. The locking member also works in concert with an interlocking sleeve which prevents activation of the injector when the nozzle is removed therefrom. The safety mechanism also includes a feature for automatically returning the locking member to a locked position after activation.

21 Claims, 11 Drawing Sheets

U.S. PATENT DOCUMENTS

| | | |
|---|---|---|
| 2,800,903 | 7/1957 | Smoot . |
| 2,816,543 | 12/1957 | Venditty et al. . |
| 2,816,544 | 12/1957 | Scherer et al. . |
| 2,820,655 | 1/1958 | Hileman . |
| 2,821,193 | 1/1958 | Ziherl et al. . |
| 2,821,981 | 2/1958 | Ziherl et al. . |
| 2,825,332 | 3/1958 | Johnson . |
| 2,902,994 | 9/1959 | Scherer . |
| 2,921,582 | 1/1960 | Sadd . |
| 2,928,390 | 3/1960 | Venditty et al. . |
| 3,057,349 | 10/1962 | Ismach . |
| 3,066,670 | 12/1962 | Stauffer . |
| 3,115,133 | 12/1963 | Morando . |
| 3,123,070 | 3/1964 | Kath . |
| 3,129,708 | 4/1964 | Krantz . |
| 3,130,723 | 4/1964 | Venditty et al. . |
| 3,131,692 | 5/1964 | Love . |
| 3,138,157 | 6/1964 | Ziherl et al. . |
| 3,140,713 | 7/1964 | Ismach . |
| 3,147,967 | 9/1964 | Bougeard . |
| 3,167,071 | 1/1965 | Venditty . |
| 3,189,029 | 6/1965 | Stephens . |
| 3,202,151 | 8/1965 | Kath . |
| 3,245,703 | 4/1966 | Manly . |
| 3,292,622 | 12/1966 | Banker . |
| 3,308,818 | 3/1967 | Rutkowski . |
| 3,330,276 | 7/1967 | Gordon . |
| 3,330,277 | 7/1967 | Gabriels . |
| 3,335,722 | 8/1967 | Lowry et al. . |
| 3,353,537 | 11/1967 | Knox et al. . |
| 3,399,759 | 9/1968 | Love . |
| 3,406,684 | 10/1968 | Tsujino . |
| 3,424,154 | 1/1969 | Kinsley . |
| 3,461,867 | 8/1969 | Zimmet et al. . |
| 3,476,110 | 11/1969 | Yahner . |
| 3,490,451 | 1/1970 | Yahner . |
| 3,507,276 | 4/1970 | Burgess . |
| 3,518,990 | 7/1970 | Banker . |
| 3,521,633 | 7/1970 | Yahner . |
| 3,526,225 | 9/1970 | Isobe . |
| 3,527,212 | 9/1970 | Clark . |
| 3,557,784 | 1/1971 | Shields . |
| 3,561,443 | 2/1971 | Banker . |
| 3,625,208 | 12/1971 | Frost et al. . |
| 3,659,587 | 5/1972 | Baldwin . |
| 3,688,765 | 9/1972 | Gasaway . |
| 3,714,943 | 2/1973 | Yanof et al. . |
| 3,768,472 | 10/1973 | Hodosh et al. . |
| 3,779,371 | 12/1973 | Rovinski . |
| 3,782,380 | 1/1974 | Van Der Gaast . |
| 3,783,895 | 1/1974 | Weichselbaum . |
| 3,788,315 | 1/1974 | Laurens . |
| 3,805,783 | 4/1974 | Ismach . |
| 3,827,601 | 8/1974 | Magrath et al. . |
| 3,838,689 | 10/1974 | Cohen . |
| 3,908,651 | 9/1975 | Fudge . |
| 3,938,520 | 2/1976 | Scislowicz et al. . |
| 3,945,379 | 3/1976 | Pritz et al. . |
| 3,945,383 | 3/1976 | Bennett et al. . |
| 4,059,107 | 11/1977 | Iriguchi et al. . |
| 4,089,334 | 5/1978 | Schwebel et al. . |
| 4,328,802 | 5/1982 | Curley et al. . |
| 4,387,879 | 6/1983 | Tauschinski . |
| 4,421,508 | 12/1983 | Cohen . |
| 4,447,225 | 5/1984 | Taff et al. . |
| 4,500,075 | 2/1985 | Tsuchiya et al. . |
| 4,505,709 | 3/1985 | Froning et al. . |
| 4,507,113 | 3/1985 | Dunlap . |
| 4,518,385 | 5/1985 | Lindmayer et al. . |
| 4,561,856 | 12/1985 | Cochran . |
| 4,588,403 | 5/1986 | Weiss et al. . |
| 4,596,556 | 6/1986 | Morrow et al. ......................... 604/70 |
| 4,619,651 | 10/1986 | Kopfer et al. . |
| 4,623,332 | 11/1986 | Lindmayer et al. . |
| 4,626,242 | 12/1986 | Fejes et al. . |
| 4,662,878 | 5/1987 | Lindmayer . |
| 4,675,020 | 6/1987 | McPhee . |
| 4,680,027 | 7/1987 | Parsons et al. . |
| 4,709,686 | 12/1987 | Taylor et al. . |
| 4,722,728 | 2/1988 | Dixon . |
| 4,744,786 | 5/1988 | Hooven . |
| 4,768,568 | 9/1988 | Fournier et al. . |
| 4,771,758 | 9/1988 | Taylor et al. . |
| 4,775,173 | 10/1988 | Sauer . |
| 4,790,824 | 12/1988 | Morrow et al. . |
| 4,834,149 | 5/1989 | Fournier et al. . |
| 4,850,967 | 7/1989 | Cosmai . |
| 4,863,427 | 9/1989 | Cocchi . |
| 4,874,367 | 10/1989 | Edwards . |
| 4,883,483 | 11/1989 | Lindmayer . |
| 4,909,488 | 3/1990 | Seibert et al. . |
| 4,923,072 | 5/1990 | Rilliet . |
| 4,940,460 | 7/1990 | Casey et al. . |
| 4,941,880 | 7/1990 | Burns . |
| 4,948,104 | 8/1990 | Wirges . |
| 4,989,905 | 2/1991 | Rajecki . |
| 5,024,656 | 6/1991 | Gasaway et al. ......................... 604/70 |
| 5,031,266 | 7/1991 | Tillman et al. . |
| 5,041,715 | 8/1991 | Muller . |
| 5,052,725 | 10/1991 | Meyer et al. . |
| 5,061,263 | 10/1991 | Yamazaki et al. . |
| 5,062,830 | 11/1991 | Dunlap . |
| 5,064,413 | 11/1991 | McKinnon et al. . |
| 5,066,280 | 11/1991 | Braithwaite . |
| 5,073,165 | 12/1991 | Edwards . |
| 5,085,332 | 2/1992 | Gettig et al. . |
| 5,116,313 | 5/1992 | McGregor . |
| 5,135,507 | 8/1992 | Haber et al. . |
| 5,161,786 | 11/1992 | Cohen . |
| 5,165,560 | 11/1992 | Ennis, III et al. . |
| 5,176,406 | 1/1993 | Straghan . |
| 5,190,523 | 3/1993 | Lindmayer . |
| 5,193,517 | 3/1993 | Taylor et al. . |
| 5,209,362 | 5/1993 | Lutzker . |
| 5,224,932 | 7/1993 | Lappas . |
| 5,226,882 | 7/1993 | Bates . |
| 5,292,308 | 3/1994 | Ryan . |
| 5,304,128 | 4/1994 | Haber et al. . |
| 5,312,335 | 5/1994 | McKinnon et al. . |
| 5,312,577 | 5/1994 | Peterson et al. . |
| 5,316,198 | 5/1994 | Fuchs et al. . |
| 5,334,144 | 8/1994 | Alchas et al. . |
| 5,356,380 | 10/1994 | Hoekwater et al. . |
| 5,360,146 | 11/1994 | Ikushima . |
| 5,383,851 | 1/1995 | McKinnon, Jr. et al. . |
| 5,399,163 | 3/1995 | Peterson et al. . |
| 5,407,431 | 4/1995 | Botich et al. . |
| 5,423,756 | 6/1995 | Van der Merwe . |
| 5,480,381 | 1/1996 | Weston ...................... 604/68 |
| 5,499,972 | 3/1996 | Parsons ...................... 604/68 |
| 5,503,627 | 4/1996 | McKinnon et al. ....... 604/72 |
| 5,520,639 | 5/1996 | Peterson et al. .......... 604/68 |
| 5,569,189 | 10/1996 | Parsons ...................... 604/68 |

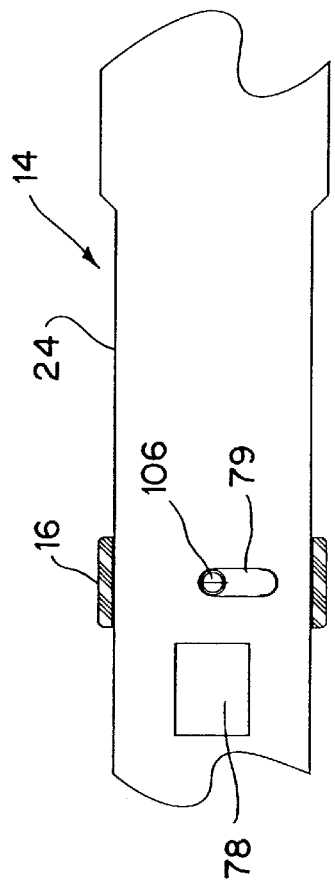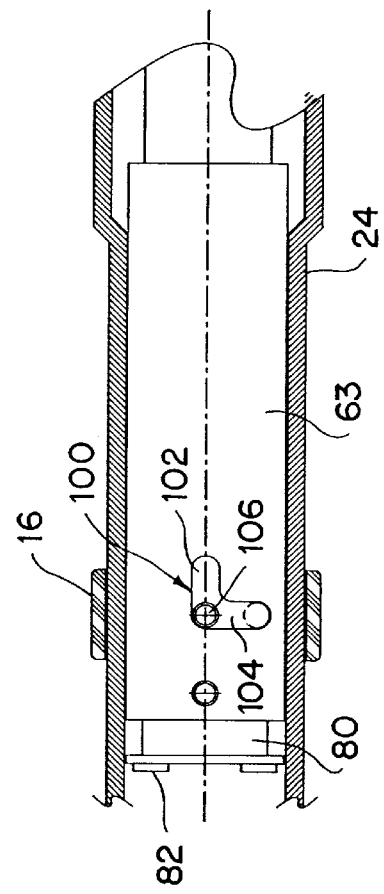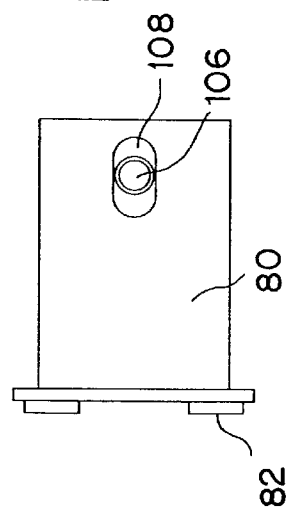

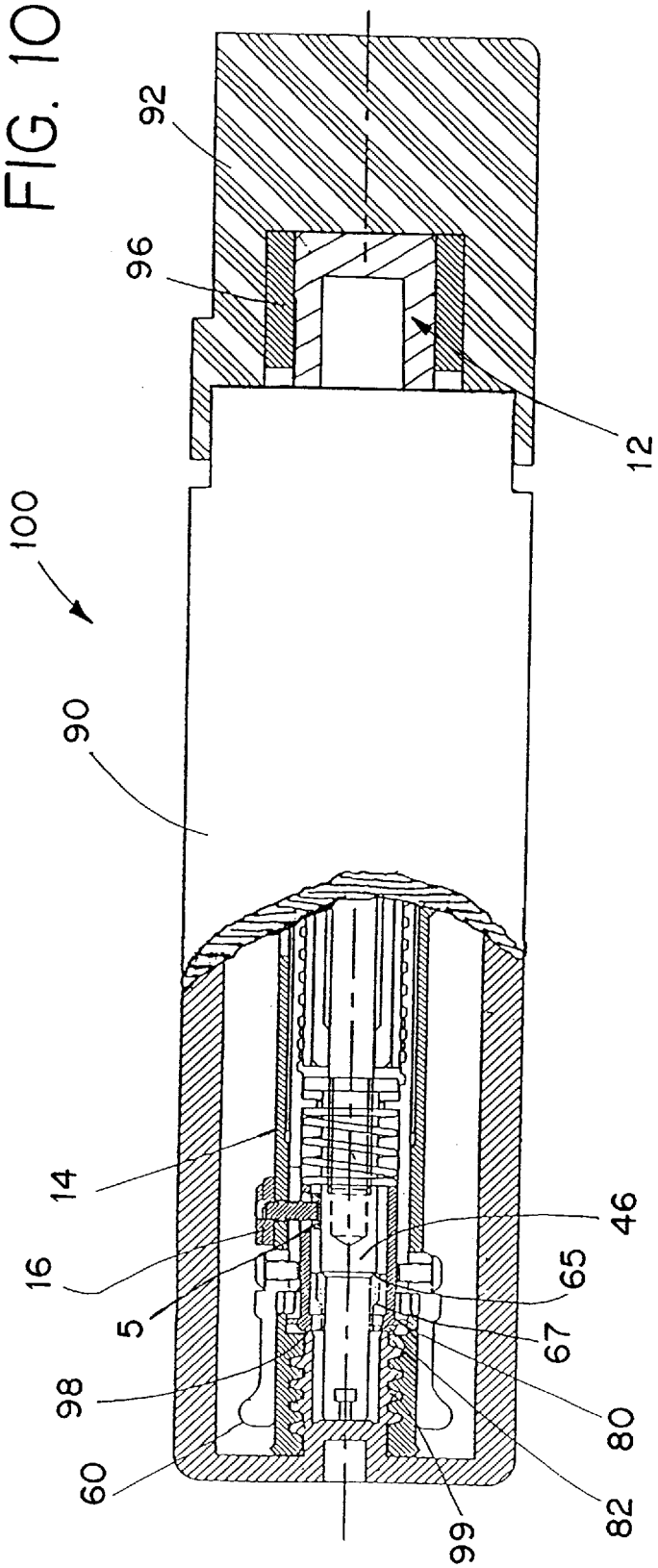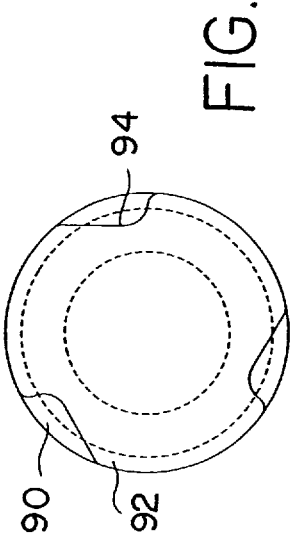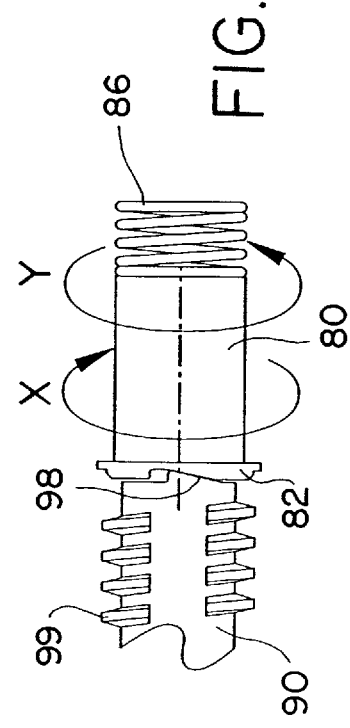

SAFETY MECHANISM FOR INJECTION DEVICES

FIELD OF THE INVENTION

The present invention generally relates to a needleless fluid injection apparatus. More particularly, the present invention relates to a safety mechanism to aid in prevention of accidental discharges of fluid from the apparatus.

BACKGROUND OF THE INVENTION

Needleless hypodermic injection devices have been known and used in the past. These devices typically use spring or compressed gas driven plungers to accelerate a fluid at a velocity sufficient to pierce the skin and enter the underlying tissues.

Since at least the 1980s, the use of needleless injectors has become more desirable due to concerns over the spread of AIDS, hepatitis and other viral diseases caused by the possibility of accidental needle "sticks" from the conventional syringe and needle. Needleless injectors remove apprehensions of healthcare workers and are superior in eliminating accidental disease transmission.

A number of different needleless injectors are known including U.S. Pat. No. 5,062,830 to Dunlap, U.S. Pat. No. 4,790,824 to Morrow et al., U.S. Pat. No. 4,623,332 to Lindmayer et al., U.S. Pat. No. 4,421,508 to Cohen, U.S. Pat. No. 4,089,334 to Schwebel et al., U.S. Pat. No. 3,688,765 to Gasaway, U.S. Pat. No. 3,115,133 to Morando, U.S. Pat. No. 2,816,543 to Venditty, et al., and U.S. Pat. No. 2,754,818 to Scherer. These injectors typically include a nozzle assembly, which includes a medication holding chamber and a piston. The chamber has an orifice through which a jet of medication is forced out of the chamber using the piston actuated by some type of energy source.

Due to the high velocity of the jet created by the typical needleless injector, it is desirable to prevent premature discharges of the energy source. Thus, there is a need for a needleless injector which remains in the unarmed or locked configuration until the time period when activation is desired.

SUMMARY OF THE INVENTION

It is, therefore, an object of the present invention to prevent premature or unwanted discharges of the energy source of an injection device by incorporating safety mechanisms. It is desirable to provide safety mechanisms which have relatively few parts and which are easily activated and deactivated by the user.

It is an object to provide a safety mechanism which prevents unwanted or inadvertent activation of the injection device when a nozzle is installed thereon. It is also an object to provide a safety mechanism which prevents activation of the injection device when the nozzle has been removed from the injector body. It is a further object to provide a safety which is incapable of being deactivated when there is no nozzle installed on the device. It is a further object to provide a safety mechanism that is capable of being deactivated when a nozzle is installed onto the injection device.

Yet another object of the present invention is to provide a safety mechanism which works in conjunction with an arming device to lock the injection device after the injection device has been armed prior to installation of a nozzle.

It is a further object of the present invention to provide a safety mechanism which automatically returns to a locked position after the injector has been discharged and rearmed prior to installation of a nozzle thereon.

Accordingly, the present invention relates to a safety mechanism adapted for an injection device, such as a needleless injection device which has a housing which includes a fluid chamber at least partially disposed therein and an energy generating source. The safety mechanism includes a triggering member disposed within the housing and operatively associated with the energy generating source so that movement of the triggering member activates the energy source to expel a fluid from the fluid chamber; and a locking member disposed on the exterior of the housing and operatively associated with the triggering member. The locking member is movable between a locked position and an unlocked position, wherein movement of the triggering member is prevented when the locking member is in the locked position, and wherein movement of the triggering member is possible when the locking member is in the unlocked position. A nozzle associated with the housing and defining the fluid chamber therein can be included as an integral or disposable component of this device, and a biasing member for urging the locking member toward the locked position is advantageous.

Preferably, the housing and triggering member each have an aperture disposed thereon and the locking member has a protruding lug which projects inwardly through the housing aperture and extends into the triggering member aperture, with the lug being moveable within each of the apertures. The housing and triggering member apertures may be elongated with the locked and unlocked positions being configured and arranged such that longitudinal movement of the triggering member is possible when the locking member is in the unlocked position but not when the locking member is in the locked position.

The triggering member may be a cylindrical trigger sleeve disposed within the housing, while the locking member extends at least partially along an exterior surface of the housing. In a preferred embodiment, the locking member comprises a ring rotationally disposed on the exterior of the housing. In this embodiment, it is useful to configure the elongated aperture of the triggering member to be L-shaped, with a first segment of the aperture extending transversely while a second segment of the aperture extends longitudinally with respect to the triggering member. This allows the locking member to be in the locked position when the lug is disposed in the transverse segment of the aperture, and to be in the unlocked position when the lug is disposed in the longitudinal segment of the aperture.

The biasing member is preferably a helical spring for urging the locking member both longitudinally and rotationally so that the locking member is biased into the locked position when the injector is armed. The trigger sleeve may also include at least one release member operatively associated therewith which is engageable to move the trigger sleeve to activate the energy generating source.

In one arrangement, the release member is a pad which is disposed on the exterior of the housing and operatively connected to the trigger sleeve. This pad is longitudinally moveable to correspondingly move the trigger sleeve to activate the energy generating source. Alternatively, the release member comprises a button and a blocking member operatively associated with both the button and the trigger sleeve. Here, the trigger sleeve is distally biased by the energy generating source, the blocking member blocks the distal movement of the trigger sleeve when the button is in a non-depressed state, and depression of the button moves the blocking member transversely, thereby allowing the trigger sleeve to move distally to activate the energy source. The blocking member may be integrally formed with the button, and be in the form of a ring disposed within the interior of the housing, the ring having an opening dimensioned and configured for receiving a portion of the trigger sleeve.

The trigger sleeve can further include an extension associated at its distal end, with the extension being in blocking relation with the blocking member when the release member button is in the non-depressed state, yet being disengagable from the blocking member when the release member button is depressed to allow distal movement of the trigger sleeve to activate the energy source.

Another useful addition is an interlock sleeve which is rotationally coupled with the locking member and which has an aperture therein for receiving the lug. This interlock sleeve can be biased distally by a second biasing member, typically in the form of a separate or integrally formed spring. The interlock sleeve may have disposed thereon one or more raised surfaces while the housing, at its distal end, includes a plurality of teeth so that the second biasing member biases the raised surface(s) of the interlock sleeve into engagement with the teeth to prevent rotational movement of the interlock sleeve.

For these embodiments, a disposable nozzle, which defines the fluid chamber therein, is operatively associated with the interlock sleeve such that when the nozzle is removed from the housing, the interlock sleeve is biased by the second biasing member into rotational locking engagement with the housing while the installation of the nozzle in an operative position causes the nozzle to move the interlock sleeve proximally out of engagement with the housing. When the second biasing member is a helical spring for biasing the interlock sleeve longitudinally into locking relationship, this spring may be compressed when the nozzle is installed so that the raised surface(s) on the interlock sleeve is moved out of locking engagement with the teeth disposed on the housing.

Finally, the safety mechanism may also include an arming device including a housing, preferably configured as a tube, and a cap which is removably and circumferentially disposed about the housing of the injector. In this embodiment, the tube may be configured and dimensioned for receiving a distal end of the housing, while the cap may be configured and dimensioned for receiving a proximal end of the energy generating source. Thus, when the nozzle is removed from the injector after the energy generating source has been fired, the tube is attached to the housing and the cap is rotated to arm the energy generating source.

This tube may include an inwardly protruding portion located at its distal end for engaging the distal end of the housing, with this inwardly protruding portion being configured and dimensioned for receiving the distal end of the housing after the nozzle has been removed therefrom so that as the inwardly protruding portion is attached to the housing, a proximal end of the inwardly protruding portion displaces the interlock sleeve proximally out of locking engagement with the housing. The proximal end of the inwardly protruding portion preferably has disposed thereon a plurality of ramps and steps while the distal end of the interlock sleeve has disposed thereon a plurality of ramps and steps configured and dimensioned for coupling with the proximal end of the inwardly protruding portion, wherein when the tube engages the distal end of the housing, the ramps interact to push the interlock sleeve out of locking engagement with the housing and, after the injector has been armed by rotating the cap, as the tube is removed from the distal end of the housing, the steps couple to rotate the interlock sleeve to position the locking member in the locked position.

Yet another embodiment of the safety mechanism includes a lug disposed on the locking member, an interlock sleeve disposed beneath the triggering member within the housing and having an aperture disposed thereon, and a biasing member for normally retaining the locking member in the locked position. Each of the housing and triggering member advantageously has an aperture disposed thereon so that the lug can project inwardly through the housing aperture and extend into the triggering member aperture, where it is slideable within each aperture. The interlock sleeve is rotationally operatively associated with the locking member via the lug, with the lug also extending into and being slideably engaged in the interlock sleeve aperture. The biasing member is attached to the triggering member in a non-rotational manner at its proximal end and attached to the interlock sleeve for rotation with the interlock sleeve at its distal end. Thus, after the locking member has been moved into the unlocked position and the energy generating source is fired and the energy generating source is armed, the locking member is biased by the biasing member into the locked position.

BRIEF DESCRIPTION OF THE DRAWINGS

Preferred features of the present invention are disclosed in the accompanying drawings, wherein similar reference characters denote similar elements throughout the several views, and wherein:

FIG. 6 is a partial elevated view of the housing of the needleless injector incorporating one embodiment of the safety mechanism of the present invention;

FIG. 7 is a partial cross-sectional view of the needleless injector showing the trigger sleeve incorporating the safety mechanism of the present invention;

FIG. 8 is an elevated view of the interlocking sleeve of a needleless injector incorporating a safety mechanism of the present invention;

FIG. 10 is a partial cross-sectional view of a needless injector incorporating another embodiment of the safety mechanism of the present invention installed in an arming device;

FIG. 11 is a proximal end view of the arming device shown in FIG. 10;

FIG. 12 is an elevated view of the interlock sleeve engaged with the arming device;

DETAILED DESCRIPTION OF THE PREFERRED EMBODIMENTS

Figure 1:
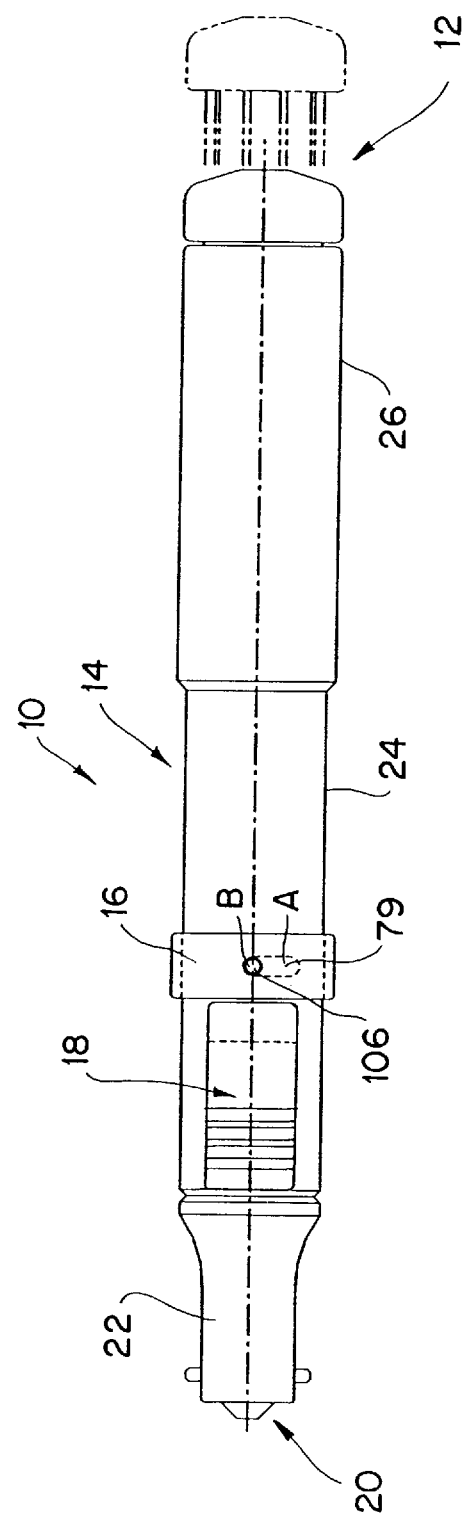
FIG. 1 is an elevated view of one embodiment of the safety mechanism of the present invention incorporated into a needleless injector.

Referring to FIG. 1, the exterior of a typical needleless injector is shown with one embodiment of the safety device of the present invention installed thereon. Needleless injector 10 includes a power unit 12, a housing 14, a locking member 16, a trigger assembly 18, and a nozzle assembly 20.

The triggering assembly 18 is operatively connected to power unit 12 so that movement of the triggering assembly activates the power unit 12. When the power unit 12 is activated, it expels energy toward the nozzle assembly 20. Locking member 16 serves as a safety mechanism by limiting movement of the triggering assembly 18.

The locking member may take on many forms including a ring, a semi-circle, a paddle, a button, and the like. Several embodiments of the locking member are depicted herein for illustration purposes. Locking members of other shapes will be readily apparent to those skilled in the art and the depicted embodiments should not be considered restrictively.

A locking member in the shape of a lock ring 16 is shown in FIG. 1. Lock ring 16 is rotationally movable by a user between a position "A" and a position "B". Position "A", as depicted in FIG. 1, is a locked position where the triggering assembly 18 is stationary and unable to trigger the release of energy from power unit 12. Position "B", as depicted in FIG. 1, is an unlocked position where the triggering assembly 18 is movable distally to trigger the release of energy from the power unit 12.

As used in this application, the terms distal or front shall designate the end or direction toward the nozzle assembly 20 of the injector 10. The terms proximal or rear shall designate the end or direction toward the power unit 12. The term longitudinal designates an axis connecting nozzle assembly 20 to power unit 12, and the term transverse designates a direction substantially perpendicular to the longitudinal direction including arcs along the surface of housing member 14.

Figure 2:
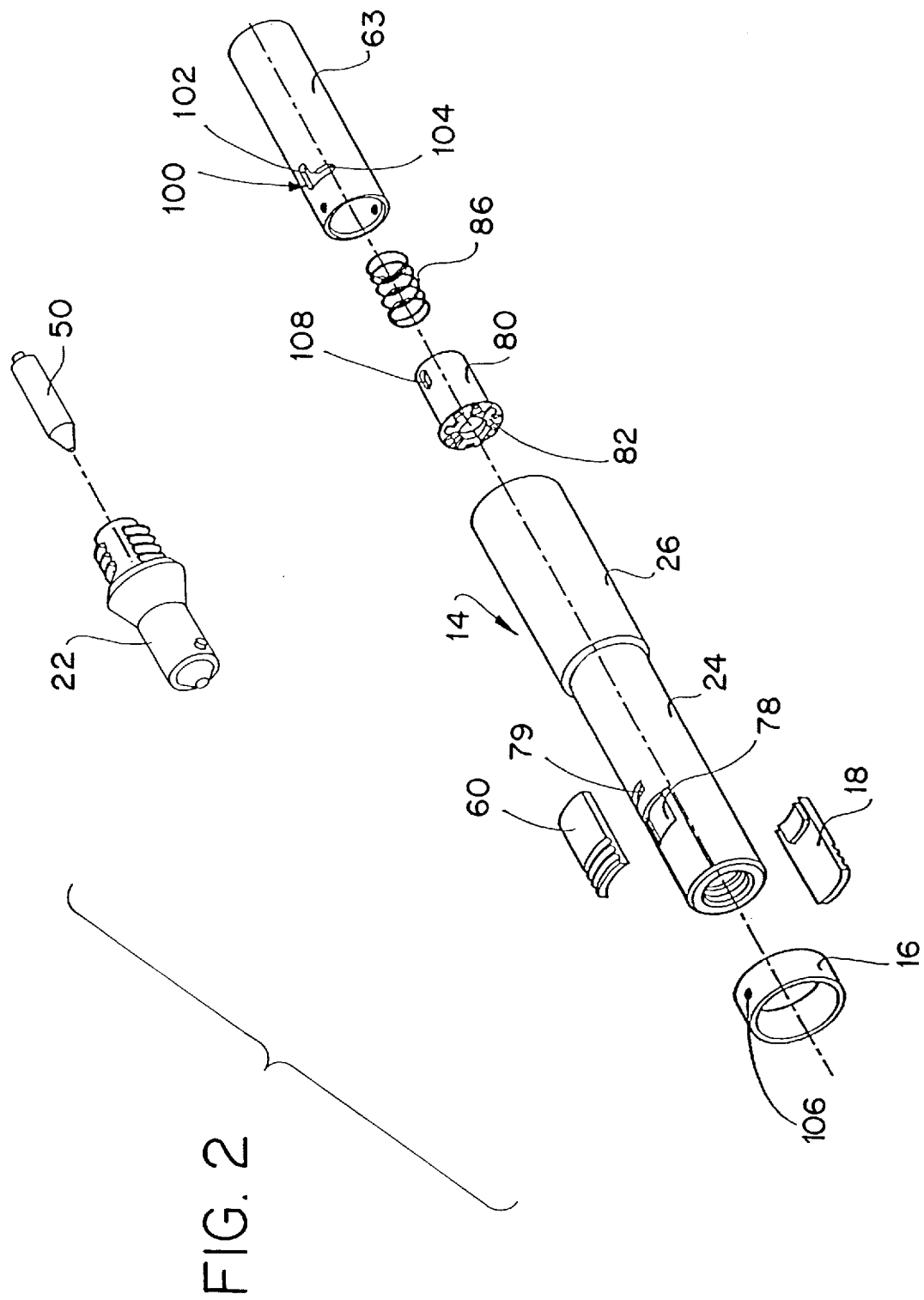
FIG. 2 is a partial exploded view of the needleless injector showing the nozzle, the housing and one embodiment of the safety mechanism of the present invention.
Figure 3:
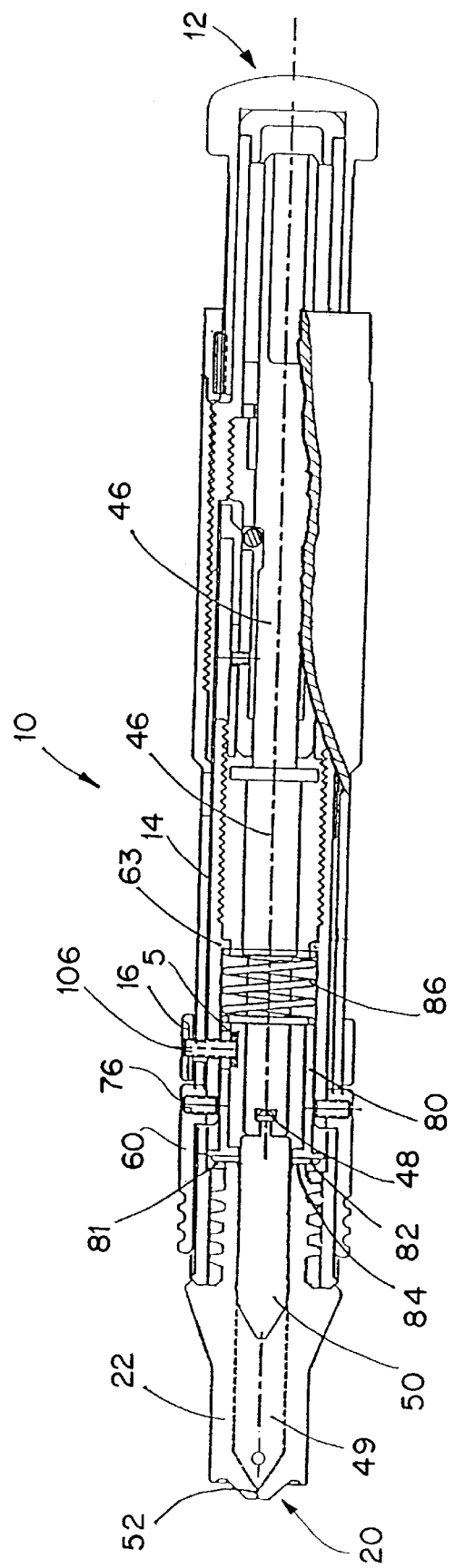
FIG. 3 is a cross-sectional view of a needleless injector incorporating a safety mechanism of the present invention prior to ejection of the medicament from the injector.

As shown in FIGS. 2 and 3, nozzle assembly 20 includes a main body 22, a piston 50, and a chamber 49 defined to hold the medicament to be ejected therefrom. The plunger 50 is slideably disposed in chamber 49 and contoured to fit within chamber 49. Nozzle assembly 20 preferably includes conventional threads or bayonet mounts for removably connecting nozzle assembly 20 to needleless injector 10. The nozzle assembly 20 can be disposable or reusable.

The main body of the injector 10 is comprised of housing 14. Housing 14 may include a front region 24 and a back region 26. The power unit 12 is generally installed in the back region 26 while the ram mechanism, also known as a plunger 46, extends from back region 26 into front region 24 of housing 14.

Figure 4:
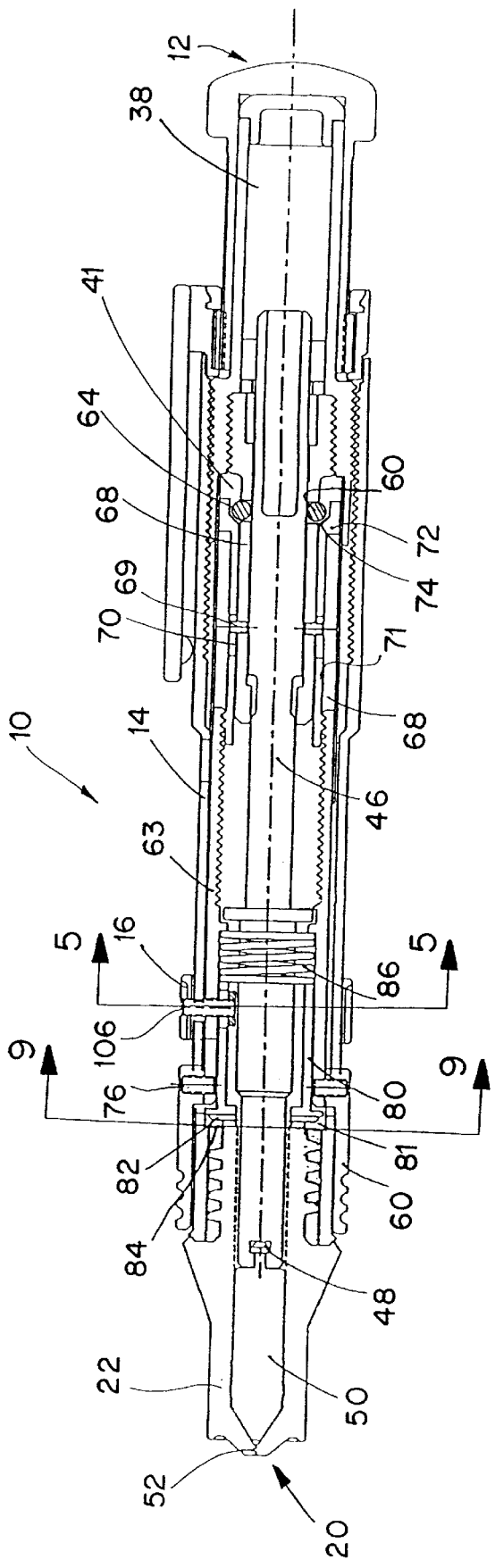
FIG. 4 is a cross-sectional view of a needleless injector incorporating a safety mechanism of the present invention after discharge of the medicine from the injector.

The power unit 12 may be in either a relaxed or armed state or an energized or unarmed state. The relaxed state is shown in FIG. 4 while the energized state is shown in FIG. 3. The energized state generally describes a situation where a coil spring has been compressed or where gas contained in a gas spring has been compressed to store energy therein. In the relaxed state, the energy stored in the power unit 12 has been expanded to drive the plunger 46 and medicament out of nozzle 22, i.e., the coil spring or compressed gas has been expended.

The type of energy source depicted in FIGS. 2, 3, and 4 can be characterized as a gas spring. However, the safety mechanisms described herein are contemplated for use with any type of energy generating source including a coil spring, a gas spring, a gas cartridge, a hydraulic ram, a compressor, or the like. In that the invention described herein resides primarily in the safety mechanisms associated with locking member 16, it is not believed necessary to describe in great detail the construction or operation of the energy generating source, as this component is not critical to the operation of the present invention. A typical injection device is described in co-pending U.S. application Ser. No. 08/369,812, the contents of which is incorporated herein by reference.

Figure 18:
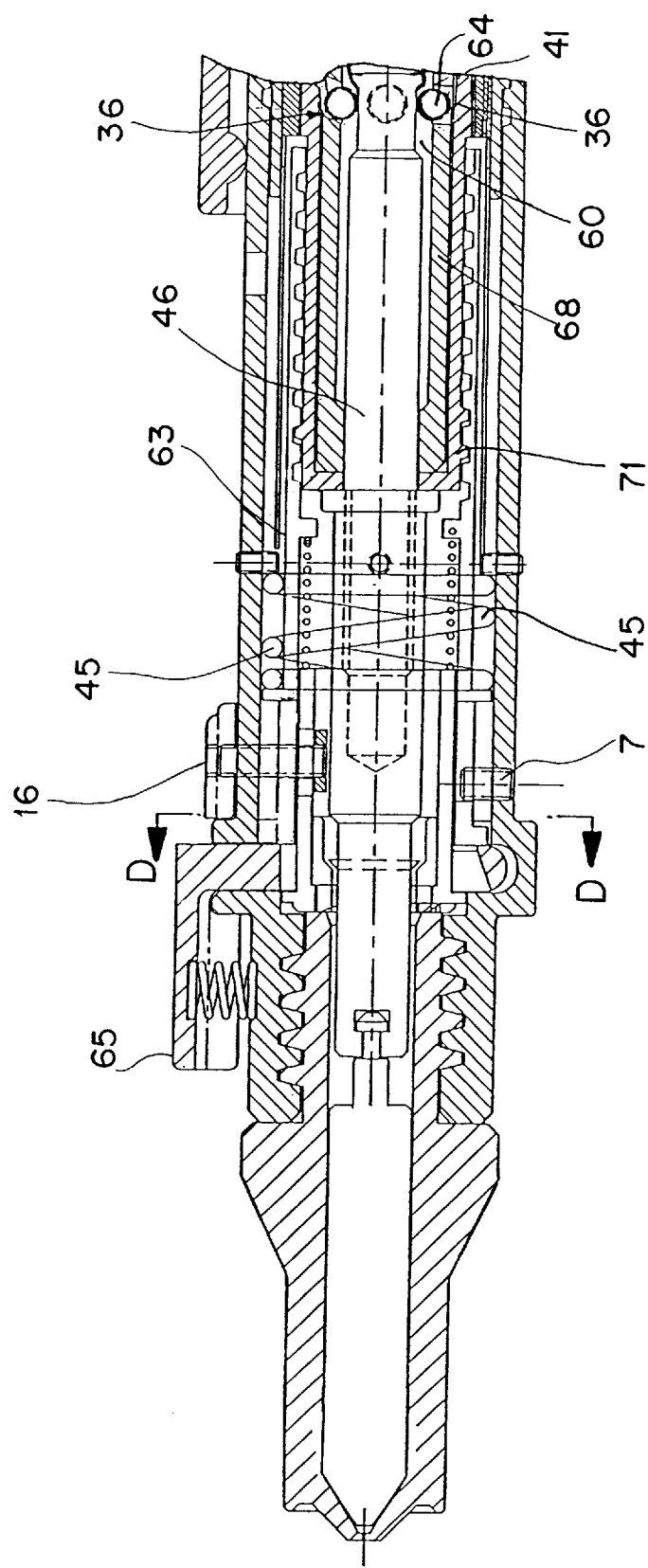
FIG. 18 is an enlarged cross-sectional view of the embodiment shown in FIG. 17 showing the distal end of the injector incorporating another embodiment of the firing mechanism of the present invention.

Referring again to FIGS. 2, 3 and 4, the triggering assembly 18 is adapted to retain the power unit 12 in its energized state until activation is desired and comprises a triggering mechanism capable of releasing the energy stored in the power unit 12. The triggering assembly 18 includes a trigger sleeve 63 which is preferably connected to release members 60 via connectors 76. Release members 60 are depicted as pads which are slidingly received on front portion 24 of housing member 14. Triggering sleeve 63 engages the power unit 12 in the back portion 26 of housing 14. A pin 7, as shown in FIG. 18, may preferably be disposed in the housing and extends into the trigger sleeve in order to keep the trigger sleeve from rotating within the housing.

Front portion 24 defines first openings 78. First openings 78 are configured and dimensioned for connectors 76 to connect trigger sleeve 63 to release members 60, and for release members 60 to slide forward relative to front portion 24 to trigger the power unit 12 to expel energy, FIG. 3 shows the release members 60 in a position prior to activation of the triggering assembly. FIG. 4 shows the release members 60 in a position after energy has been expelled from the power unit 12.

Needleless nozzle assembly 20 is attached to housing 14 at the distal end, as shown in FIGS. 2, 3 and 4. The nozzle assembly 20 includes main body 22 and piston 50. Medicament may be drawn into chamber 49 of main body 22 through orifice 52. Medicament may also be expelled through orifice 52 when the injector 10 is activated. Nozzle body 22 may be affixed to injector 10 with any type of mounting mechanisms that are capable of withstanding the force generated by the power unit 12, e.g., threads, bayonet mounts, or the like. Nozzle assembly 20 may be removably connected to housing 14 of injector 10 through these mounting mechanisms.

Referring again to FIGS. 3 and 4, a plunger 46 is slidingly received within housing 14. The plunger 46 is received within power unit 12 at the proximal end of housing 14. Once armed, plunger 46 is capable of sliding in the longitudinal direction within injector 10 without forcing the energy stored in power unit 12 to be expelled, i.e., the plunger 46 remains locked in the compressed state even as the power unit 12 moves. Plunger 46 extends substantially along the length of housing 14. At its distal end, it contains connector 48 for affixing to piston 50 of nozzle assembly 20.

Referring to FIG. 4, at its proximal end, plunger 46 is received inside gas spring 38. Gas spring 38 includes guide 68 on its distal end. Guide 68 includes a plurality of holes 60 which receive a plurality of ball bearings 64. Trigger collar 71 is keyed to guide 68, or alternatively, to gas spring 38, by lug 69, so that it rotates with the gas spring, but remains free to move longitudinally. Trigger collar 71 is threadingly engaged with the trigger sleeve 63. Gas spring 38 exerts force on plunger 46, but plunger 46 is held stationary due to the blocking engagement between plunger 46, ball bearings 64 and guide 68. Therefore, unless the trigger sleeve is moved forward, plunger 46 cannot travel toward the distal end despite being pressured by gas spring 38. Thus, plunger 46 is held stationary due to the interference ball bearings 64 and guide 68.

Trigger collar 71 comprises ring 72 which blocks the movement of ball bearings 64 transversely. An annular space 41 is defined between plunger 46 and ring 72. The annular space 41 is configured and dimensioned to receive ball bearings 64. When trigger sleeve 63 is moved distally, trigger collar 71 moves distally due to their threaded engagement. As trigger collar 71 moves distally, ring 72 moves distally and out of blocking engagement with ball bearing 64. Due to the force on plunger 46 caused by gas spring 38, balls 64 are urged into annular space 41 and out of blocking engagement with guide 68. After balls 64 are removed to annular space 41, the plunger moves distally under the pressure of gas spring 38.

In another embodiment of the power unit 12, as shown in FIG. 18, plunger 46, at its proximal end, is received in gas spring 38. Gas spring 38 is attached to guide 68 on its distal end. Note that guide 68 may be integrally formed with gas spring 38. Guide 68 includes a plurality of apertures 60 which receive a plurality of ball bearings 64. Trigger collar 71 is connected rotationally to gas spring 38 so that it rotates with the gas spring but is free to move longitudinally. Trigger collar 71 retains balls 64 in position until the trigger sleeve is unlocked and free to move distally. In this embodiment, parts of which will be discussed more fully below, the trigger sleeve 63 is not attached to the release member 60. Therefore, in order to move the trigger sleeve 63 distally, the trigger sleeve 63 is urged distally by spring 45. Since trigger sleeve 63 is engaged with the trigger collar 71, preferably by a threaded connection, when the trigger sleeve moves distally, trigger collar 71 moves distally.

In operation when trigger collar 71 moves distally, it moves out of blocking arrangement with balls 64. Concurrently, the plunger 46 is under pressure from the gas spring 38 and is urged distally whenever the gas spring is changed. When trigger collar 71 moves out of blocking engagement with balls 64, balls 64 are urged transversely into annular space 41 out of blocking arrangement with plunger 46, therefore allowing the plunger 46 to move distally and the stored energy in gas spring 38 to be expelled.

Figure 17:
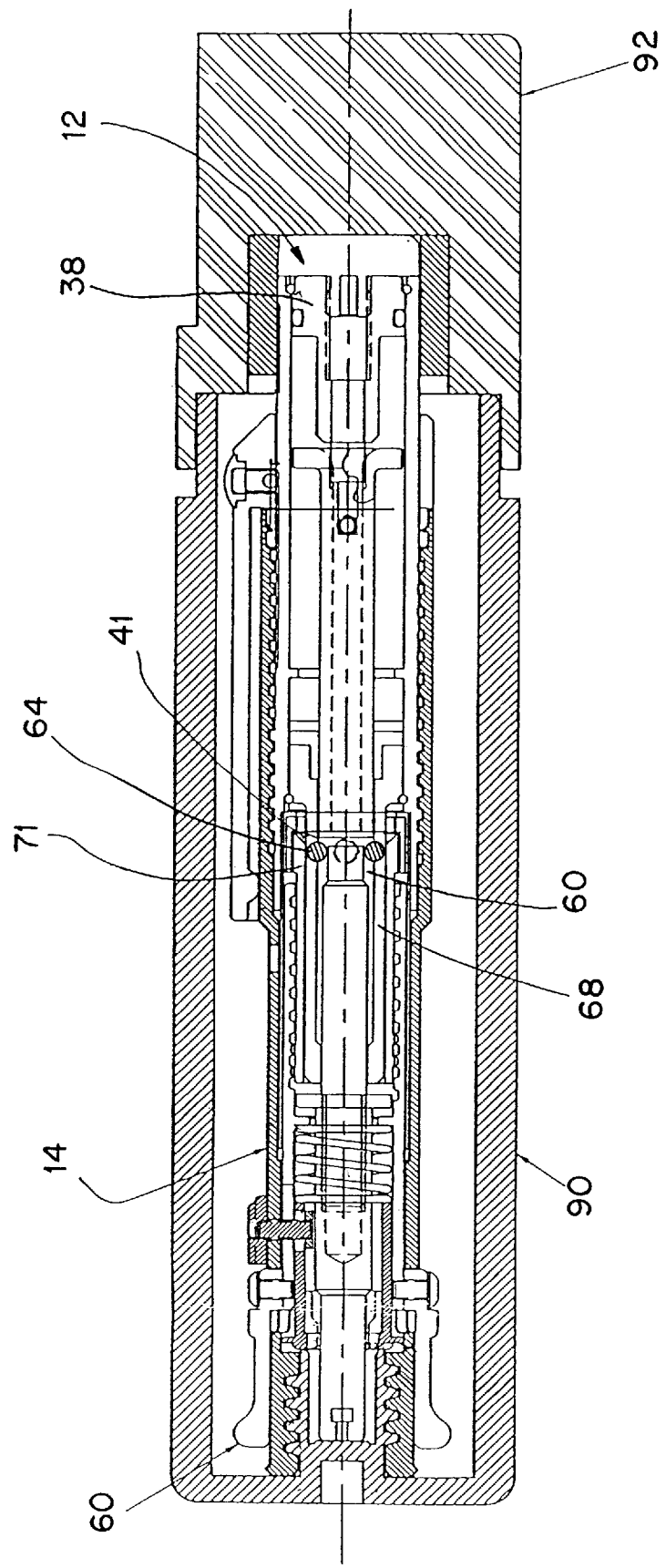
FIG. 17 is a cross-sectional view of the embodiment shown in FIG. 10 showing the injector installed in the arming device.

Advantageously, in an improvement of this embodiment, spring 45 is optional. This improved embodiment is shown in FIG. 18. In this embodiment, the improvement lies in including a ramped surface 36 on a proximal end of trigger collar 71. The ramped surface 36 may replace spring 45. When push button 65 is depressed transversely, the trigger sleeve 63 is unlocked to allow its distal movement, force put on plunger 46 by gas spring 38 pushes against balls 64. By including ramps 36, the pressure exerted against balls 64 by plunger 46 forces the balls to put pressure on the slope of the ramped surface 36, pushing the trigger collar forward. Hence, the balls are allowed to enter annular space 41 (shown entirely in FIG. 17 and partially in FIG. 18), freeing the plunger to move distally.

In operation, the injection device 10 described above may be readied for discharge, as depicted in FIG. 4, by energizing the power unit 12 and installing a nozzle assembly 20. Medicament may be drawn into chamber 49 via orifice 52 in nozzle body 22. In order to fire the device to inject the medicament into a subject, the release members 60 are moved distally. The trigger sleeve 63, being fixedly attached to release members 60, moves concurrently with release members 60 in the distal direction. Movement of trigger sleeve 63 serves to activate power unit 12 to release stored energy toward plunger 46. The stored energy released from power unit 12 drives plunger 46 in the distal direction, thereby forcing piston 50 in the distal direction. The simultaneous ramming force of the plunger 46 and piston 50 causes the medicament to be expelled forcefully from nozzle 22 through orifice 52 at a pressure sufficient to pierce the skin of the subject.

Figure 5:
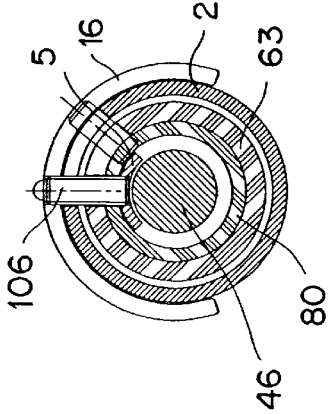
FIG. 5 is a cross-sectional view taken along line 5—5 of FIG. 4 showing one embodiment of the locking member in the unlocked position on the needleless injector.

Because of the high velocity jet created by injector 10 when activated, it is desirable to have a means for inhibiting or locking the injector in order to avoid unintentional activation or accidental discharge. Thus, it is advantageous to prevent the distal movement of release members 60 until injector 10 is properly positioned on a subject. To accomplish this, channel 100 is provided on trigger sleeve 63, which comprises a longitudinal segment 102 and a transverse segment 104, as depicted in FIG. 7. Lock ring 16 is rotationally disposed substantially on top of channel 100. A lug 106 is affixed to lock ring 16 as shown in FIGS. 3, 4 and 5 and is extended through a second channel 79 defined on housing member 14, as shown in FIG. 6, and through channel 100. Second channel 79 is preferably of a substantially similar length and width as the transverse segment of channel 100.

The locking member may also be in the form of a semi-circle, a button, a paddle, or the like. When the locking member is not disposed around the entire exterior of the housing, a means for holding the lug in position within the apertures must be provided. This may be accomplished by disposing a pin through the bottom of the lug to keep it in position. The means for holding the lug within the apertures could also be a retaining clip or the like. The embodiment being presently discussed could be used with or without a ring-shaped locking member and is shown with the ring shape in FIG. 3 with a retaining clip 5 disposed on the end of lug 106.

Referring to FIG. 1, position "A" on the exterior of housing 14 represents the locked position and corresponds to the configuration where lug 106 is disposed within transverse segment 104. When lug 106 is disposed within transverse segment 104, trigger sleeve 63 is blocked and may not be moved distally. Therefore, release members 60 are held stationary and the injector is inactivated.

To unlock injector 10, the user rotates lock ring 16 from position "A" to position "B" to move lug 106 to the intersection of transverse segment 104 and longitudinal segment 102, as shown in FIG. 7. In this configuration, trigger sleeve 63 is moveable distally to activate the injector to release the energy stored in power unit 12. Thus, position "B", as shown in FIG. 1, depicts the armed and ready position.

Figure 9:
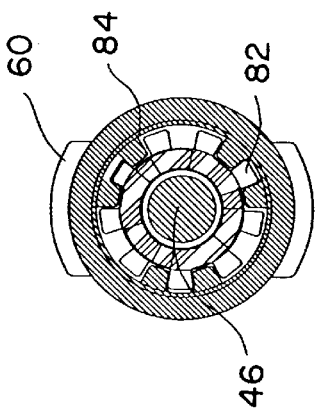
FIG. 9 is a cross-sectional view taken along line 9—9 of FIG. 4 showing the interlocking sleeve in contact with the housing of the injector.

The safety mechanism may further incorporate an interlock sleeve 80. As depicted in FIGS. 2 and 3, interlock sleeve 80 is preferably disposed internally beneath trigger sleeve 63 and housing 14. Trigger sleeve 80 is longitudinally oriented at the distal end of housing 14. With interlock sleeve 80 installed, housing 14 at the distal end preferably has a plurality of teeth 84 disposed around its internal circumference, as shown in FIG. 9.

Interlock sleeve 80 has face 82. Face 82 contains a raised surface disposed on top of a smooth surface at the distal end of sleeve 80. The raised face 82 may interlock with teeth 84 to inhibit the rotation of interlock sleeve 80 to prevent the arming of injector 10, as discussed in detail below. Interlock sleeve 80 is biased into interlocking relationship with teeth 84 by spring member 86 when nozzle assembly 20 is not attached to housing 14. When the raised surface 82 of interlock sleeve 80 is in interlocking relationship with teeth 84, it is in non-rotational locking relationship with housing 14.

Installation of nozzle assembly 20 into housing 14 displaces interlock sleeve 80 from connection with teeth 84, thereby freeing the interlock sleeve to rotate and allowing the safety mechanism to be disengaged, as will be discussed more fully below. As nozzle body 22 is pushed proximally into housing 14, it comes into contact with interlock sleeve 80 and displaces raised face 82 away from teeth 84 against the biasing force of spring 86. Installation of the nozzle assembly 20 results in the a disconnection 81 between the face 82 and the teeth 84.

The safety feature associated with the interlock sleeve 80 is created by engaging the interlock sleeve 80 with lock ring 16 via lug 106. As shown in FIG. 8, interlock sleeve 80 includes oval opening 108. Oval opening 108 is preferably approximately the same width as channel 79 of housing 14. Oval opening 108 is of sufficient size for receiving lug 106 for sliding motion in opening 108. Oval opening 108 is configured and dimensioned to allow lug 106 to move longitudinally and to allow sleeve 80 to be displaced proximally by the insertion of nozzle 22. Therefore, in this embodiment, lug 106 is received by second channel 75 in housing 14, by channel 100 in trigger sleeve 63, and by oval opening 108 in interlock sleeve 80, as depicted in FIGS. 6, 7 and 8.

In operating the safety mechanism of this embodiment, lock ring 16 works in concert with trigger assembly 18, interlock sleeve 80, and housing 14. The operation of interlock sleeve 80 is dependent upon whether the nozzle assembly 20 is installed on the housing 14 of the injection device 10. When a nozzle is removed after the device has been fired and, thus, is unarmed, the spring 86 biases the interlock sleeve 80 distally so that the teeth 84 on housing 14 are engaged by the raised surface 82 of the interlock sleeve 80. In this position, the interlock sleeve 80 may not rotate or move longitudinally and holds the lug 106 in a blocking position so that the injection device 10 may not be fired.

When a nozzle assembly 20 is installed on housing 14, the nozzle assembly 20 displaces interlock sleeve 80 in the proximal direction out of locking engagement with the housing teeth 84. When the device is armed, the interlock sleeve will rotate with the lock ring into locked state, identified as position "A" of FIG. 1. The interlock sleeve would be free to move rotationally when in this position, but is constrained by lug 106. When the user moves the lock ring 16 to the ready position, "B" in FIG. 1, lug 106 rotates interlock sleeve 86 and positions oval channel 108 substantially beneath longitudinal segment 102. In this position, the injector 10 is ready for activation. The trigger assembly may be moved distally to activate the power unit 12 to drive plunger 46 to expel the medicament from chamber 49.

As described above, unless nozzle 22 is inserted into injector 10, sleeve 80 interlocks with teeth 84 to prevent rotational movement of sleeve 80 and of lock ring 16, which is engaged with sleeve 80 via lug 106. Thus, if nozzle 22 in unattached, lock ring 16 cannot be rotated to the unlocked position and injector 10 cannot be used, thereby preventing unwanted discharges. Therefore, the use of the interlock sleeve represents another advantageous security feature of the present invention.

After the injector has been fired, in one embodiment of the present invention, the locking mechanism 16 does not automatically return to the locked position. Instead, the locking member 16 remains in the unlocked position after the device has been fired and the nozzle has been removed. In order to reactivate the injector 10, it is desirable to arm the injector 10 and to move the locking member 16 into a locked position after the device has been armed.

Therefore, as shown in FIG. 10, an arming device may be used to arm the power unit 12 of the injector 10 and to move the locking member 16 into the locked position. The arming device includes a tube 90 and a cap 92. The tube 90 may include, at the distal end, an inward protruding portion 99 which has disposed thereon threads, bayonet mounts or the like for engaging housing 14 of the injector 10. The inward protruding portion 99 engages the housing 14 in the same way as the nozzle assembly 20 engages the housing 14. Specifically, as shown in FIG. 10, bayonet mounts 99 engage the housing 14. Note that since the nozzle is disengaged, the interlock sleeve 80 will be locked into teeth 84. As the bayonet mounts are screwed into engagement with housing 14, the proximal end 98 of the inward protruding portion 99 engages the face 82 of interlock sleeve 80 and pushes the interlock sleeve out of engagement with the teeth 84.

Once the tube 90 is fixedly attached to the housing 14 of injector 10, the cap 92, as shown in FIG. 11, is disposed around the proximal end of the power unit 12. The cap is used to rotate or wind the proximal end of power unit 12 in order to arm the power unit 12. Therefore, the cap 92 must be firmly grip the proximal end of power unit 12. The cap is preferably provided with an inner collar 96 which is used to grip the proximal end of the power unit 12. The inner collar 96 is preferably a roller clutch or similar device which allows for movement in one direction only, although this is not necessary to the invention. The cap 92 may preferably have disposed thereon its exterior a plurality of knurls or grooves which aid the user in gripping the cap 92 for rotation.

Once the cap 92 has been rotated to arm the power unit 12, the cap 92 may be removed and the injector 10 may be unscrewed from the tube 90. Tube 90 includes a mechanism for placing the locking member in the locked position after the injector has been armed.

Plunger 46 includes shoulder 65 which acts in cooperation with a shoulder 67 on the interlock sleeve to act as a stop which prevents the ram from protruding past the front end of the injector when the nozzle is removed.

As shown in FIG. 12, the tube 90 has includes a surface 98 which is disposed on the proximal end of inwardly protruding portion 94. Surface 98 preferably includes a plurality of ramps and steps. The interlock sleeve 80 also preferably has a series of ramps and steps along face 82. Surface 98 and face 82 are dimensioned and configured to couple.

When injector 10 is screwed into tube 90 in the X direction of rotation, the ramps interact to push the interlock sleeve inward as the bayonets 99 are moved proximally into engagement with housing 14, thereby releasing the sleeve 80 from engagement with teeth 84 of housing 14. When injector 10 is removed from tube 90 by rotation of injector 10 in the Y direction, the steps lock together and rotate the interlock sleeve 80 in the Y direction. As interlock sleeve 80 rotates in the Y direction, the lug 106 is moved into the locked position, thereby locking the locking member. When tube 90 is removed, the interlock sleeve is again biased in the distal direction into locking relation with teeth 84 on housing 14, thereby prohibiting the locking member 16 from moving to the unlocked position and preventing unwanted discharges from the power unit 12.

In an alternative embodiment of the present invention, an automatic safety feature is employed which does not require the use of the arming device to arm the injector 10 and to lock the locking member 16. In this embodiment, lock ring 16 returns automatically to the locked "A" position after injector 10 has been armed. Preferably, the proximal end of compression spring 86 is fixedly attached to flange 58 of trigger sleeve 63. The distal end of compression spring 86 is preferably fixedly attached to the proximal end of interlock sleeve 80. In this embodiment, as lock ring 16, lug 106, and interlock sleeve 80 are rotated from the locked position "A" to the unlocked position "B", spring 86 is also rotated at its distal end but not at its proximal end, thereby storing a rotational energy within spring 86. After injector 10 is fired, the user releases lock ring 16 and lock ring 16 is biased by spring 86 to return automatically to position "A" due to the release of rotational energy by spring 86. In this embodiment, the arming device 100 is not needed. The power unit 12 is rotated by hand and, during the arming process as the triggering sleeve slides proximally, the locking member automatically moves into the locked position "A".

Figure 13:
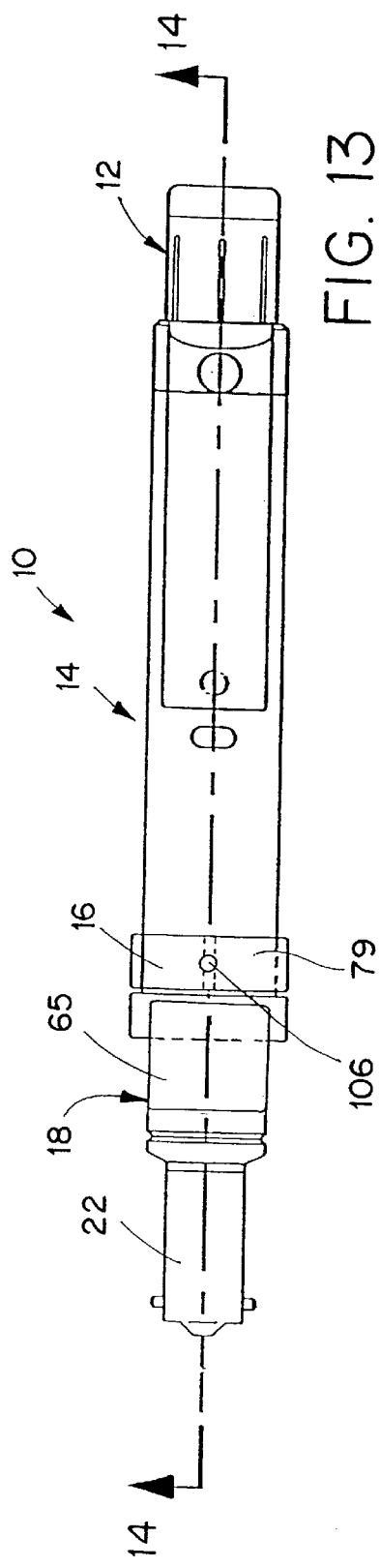
FIG. 13 is an elevated view of another embodiment showing an alternative release mechanism of the present invention incorporated into a needless injector.
Figure 14:
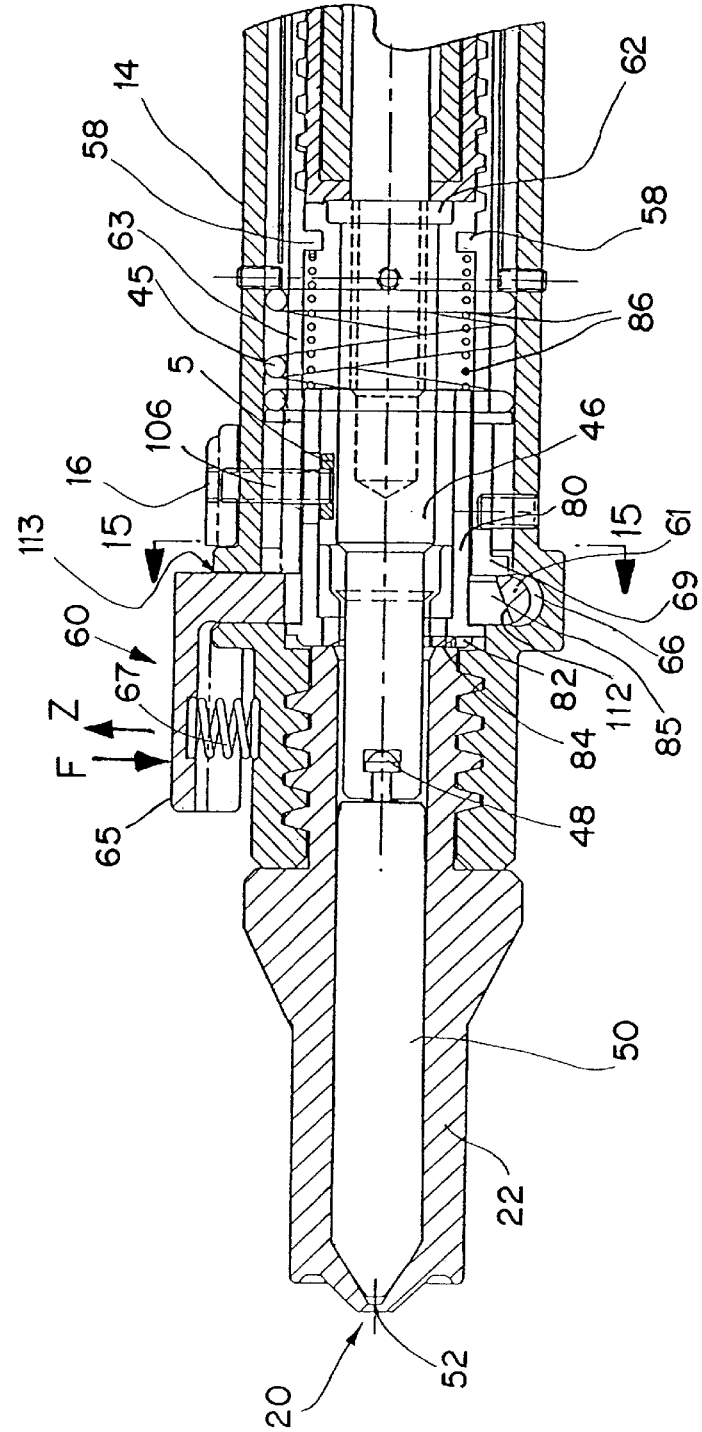
FIG. 14 is a cross-sectional view of the distal end of a needleless injector incorporating the push-button mechanism shown in FIG. 13.
Figure 15:
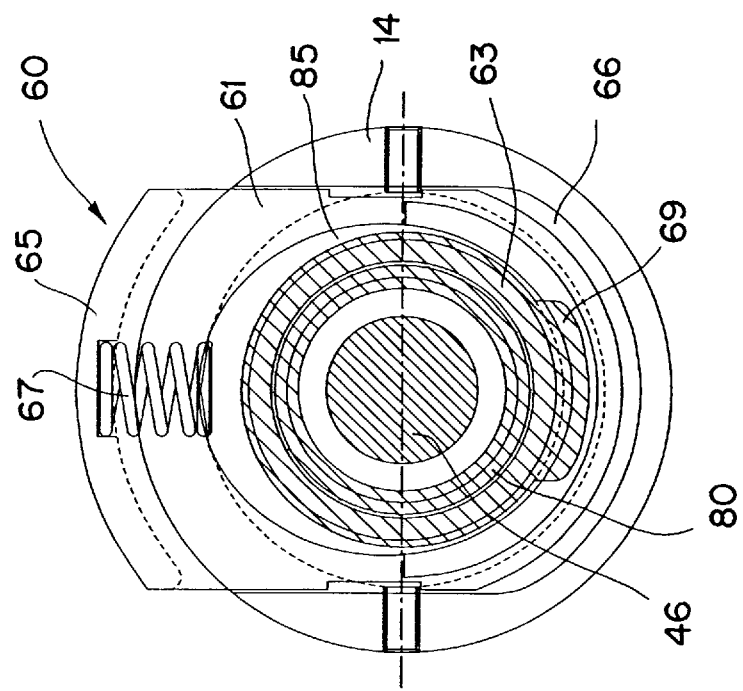
FIG. 15 is a cross-sectional view taken along line 15—15 of FIG. 14 showing the push-button embodiment of FIG. 13.

Another embodiment of the safety mechanism of the present invention is shown in FIGS. 13, 14 and 15. FIG. 13 shows an injection device 10 with a triggering assembly 18, a locking member 16, a nozzle 22, a housing 14, and a power unit 12.

In this embodiment, a locking member 16 in the shape of a semi-circle is shown. Lug 106 is attached to locking member 16. Lug 106 is retained within apertures disposed on housing 14, trigger sleeve 63, and interlock sleeve 80 by retainer clip 5. In addition to the triggering sleeve 63, triggering assembly 18 includes a release member 60 in the form of a push-button 65 which is disposed through opening 113 in housing 14 and a blocking member 61, which is integral with or fixedly attached to release member 60. Blocking member 61 is preferably in the shape of a ring and disposed internally within housing 14, although other shapes will be recognized by those skilled in the art. Blocking member 61 may be integrally formed with push-button 65 or may be connected to push-button 65 via a connector (not shown).

Referring to FIGS. 14 and 15, the locking member 16 shown is in the shape of a paddle which is disposed along the top surface of the housing 14. Locking member 16 includes lug 106 which is held in position in apertures in housing 14, trigger sleeve 63, and interlock sleeve 80 by a retainer clip 5, or the like. In this embodiment, push-button 65 is operatively associated, but not connected to trigger sleeve 63. Since push-button 65 is not connected to trigger sleeve 63, it is also not connected to the locking member 16 and may be pushed in the transverse direction F, regardless of whether the locking member is in the locked position. However, if the push-button 65 is pushed in direction F when the locking member is locked, the locking member 16 will prevent activation of the injector 10 and the action of push-button 65 in the F direction will have no effect.

The injector 10 may be activated only when the locking member 16 is in the unlocked position. In operation, when the locking member 16 is in the unlocked position and the push-button 65 is pushed in direction F so that blocking member 61 moves transversely to close gap 66, the trigger sleeve 63 moves distally into gap 85 within blocking member 61. Movement of the trigger sleeve 63 in the distal direction activates the power unit 12 to expel energy toward the nozzle 22.

The trigger sleeve 63 moves distally because it is normally biased in the distal direction by a force from spring 45. In order to avoid unwanted discharges from the injector 10 when the locking member 16 is in the unlocked position, the blocking member 61 works in concert with the triggering sleeve 63 to block the movement of the triggering sleeve 63 until the push-button is pushed in direction F. FIG. 14 shows the triggering sleeve 63 being blocked by blocking member 61. The triggering sleeve 63 preferably includes extension 69 which engages blocking member 61 until the push-button is moved in direction F.

After the injector 10 has been activated, the release member 60 is blocked from moving back to its original position due interference caused by trigger sleeve 63, i.e, after the device has fired, power unit 12 has been expelled and trigger sleeve 63 remains extended in the distal direction, thereby blocking the return of release member 60. In order to return release member 60 to its original, undepressed position, release member 60 includes spring 67. Spring 67 is disposed beneath the button 65. At its top end, spring 67 connects to the underside of button 65. At its bottom end, spring 67 connects to the exterior of housing 14. Spring 67 biases the release member in direction Z, which is opposite to direction F. As spring 67 biases button 65 in direction Z, extension 69 of trigger sleeve 63 is pushed longitudinally by a ramped surface 112 disposed on an inner surface of blocking member 61. Since the power unit 12 has been expelled, there is no longer a distal force on the triggering sleeve and the force of spring 67 forces trigger sleeve 63 out of blocking relationship with blocking member 61, thereby allowing release member 60 to return to its undepressed position.

Thereafter, the nozzle assembly 20 may be removed from the injector and the injector may be installed on tube 90 for arming. If the injector incorporates the automatic locking feature described above, then this step is not necessary and the injector may be armed by hand.

Figure 16:
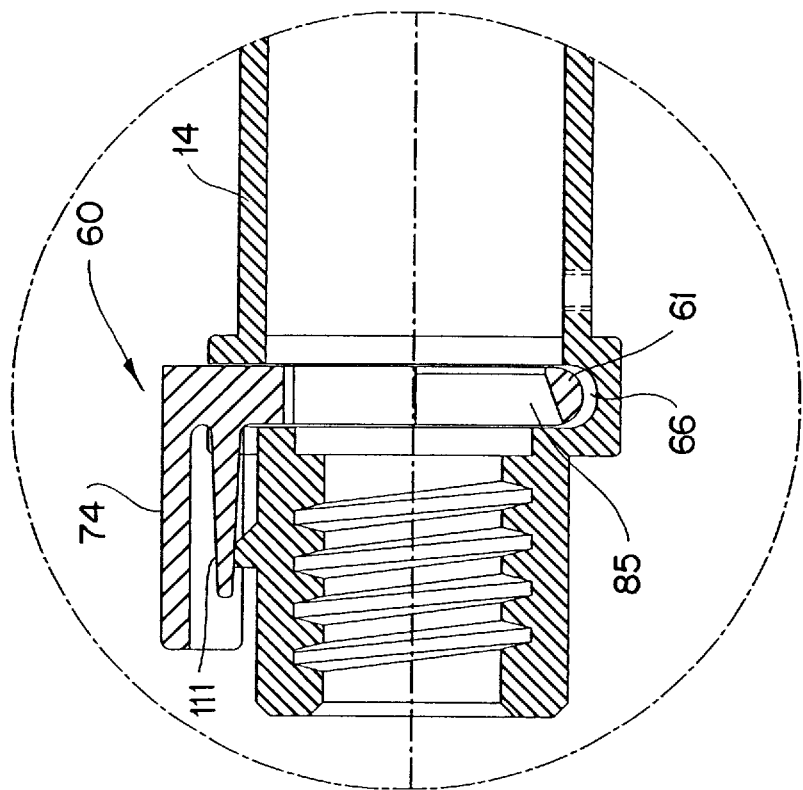
FIG. 16 is an alternative embodiment of the release mechanism of the present invention.

Referring to FIG. 16, an alternative embodiment of release member 60 is shown. In this embodiment, a push-button similar to that shown in FIGS. 14 and 15 is depicted, except that push-button 74 includes an integral spring 111 instead of an external spring 67 (as shown in FIG. 14).

While various features of the present invention were described above, it is understood that the various features of the present invention can be used singly or in any combination thereof. Therefore, this invention is not to be limited to only the specifically preferred embodiments depicted herein.

What is claimed is:

1. An injection device having a safety mechanism, wherein said injection device has a housing which includes an energy generating source and a nozzle removably associated with the housing and defining a fluid chamber therein, said safety mechanism comprising:

a triggering member disposed within the housing and operatively associated with the energy generating source so that movement of the triggering member activates the energy source to expel a fluid from the fluid chamber; and a locking member disposed on the exterior of the housing and operatively associated with the triggering member, said locking member being movable between a locked position and an unlocked position, wherein movement of the triggering member is prevented when the locking member is in the locked position, wherein movement of the triggering member is possible when the locking member is in the unlocked position and wherein the locking member can be moved to the locked or unlocked positions irrespective of whether the nozzle is associated with the housing.

2. The safety mechanism of claim 1, further comprising a biasing member for urging the locking member toward the locked position.

3. The safety mechanism of claim 1, wherein the housing and triggering member apertures are elongated and the locked and unlocked positions are configured and arranged such that longitudinal movement of the triggering member is possible when the locking member is in the unlocked position but not when the locking member is in the locked position.

4. The safety mechanism of claim 1, wherein the triggering member is a cylindrical trigger sleeve disposed within the housing.

5. The safety mechanism of claim 1, wherein the locking member extends at least partially along an exterior surface of the housing.

6. The safety mechanism of claim 1, wherein the locking member comprises a ring rotationally disposed on the exterior of the housing.

7. The safety mechanism of claim 3, wherein the elongated aperture of the triggering member is L-shaped, a first segment of said aperture extends transversely and a second segment of said aperture extends longitudinally with respect to the triggering member, wherein the locking member is in the locked position when the lug is disposed in the transverse segment of the aperture, and the locking member is in the unlocked position when the lug is disposed in the longitudinal segment of the aperture.

8. The safety mechanism of claim 2, wherein the biasing member is a helical spring for urging the locking member both longitudinally and rotationally so that the locking member is biased into the locked position when the injector is armed.

9. The safety mechanism of claim 4, wherein the trigger sleeve further comprises at least one release member operatively associated therewith, said release member being engageable to move the trigger sleeve to activate the energy generating source.

10. The safety mechanism of claim 9, wherein the release member is a pad which is disposed on the exterior of the housing and operatively connected to the trigger sleeve, said pad being longitudinally moveable to correspondingly move the trigger sleeve.

11. The safety mechanism of claim 9, wherein the release member comprises a button and a blocking member operatively associated with both the button and the trigger sleeve; said trigger sleeve is distally biased by the energy generating source; said blocking member blocks the distal movement of the trigger sleeve when the button is in a non-depressed state; and depression of the button moves the blocking member transversely, thereby allowing the trigger sleeve to move distally to activate the energy source.

12. The safety mechanism of claim 11, wherein the blocking member is integrally formed with the button, and comprises a ring disposed within the interior of the housing, said ring having an opening dimensioned and configured for receiving a portion of the trigger sleeve.

13. The safety mechanism of claim 12, wherein the trigger sleeve further comprises an extension associated with the trigger sleeve at the distal end, said extension being in blocking relation with the blocking member when the release member button is in the non-depressed state, and being disengagable from the blocking member when the release member button is depressed to allow distal movement of the trigger sleeve to activate the energy source.

14. The safety mechanism of claim 1, further comprising:

a lug disposed on the locking member, wherein the housing and triggering member each have an aperture disposed thereon and said lug projects inward through the housing aperture and extends into the triggering member aperture, said lug being slideable within each of said apertures;

an interlock sleeve disposed beneath the triggering member within the housing and having an aperture disposed thereon, said interlock sleeve being rotationally operatively associated with the locking member via the lug, said lug also extending into and being slideably engaged in the interlock sleeve aperture, and a biasing member for normally retaining the locking member in the locked position, said biasing member being attached to the triggering member in a non-rotational manner at its proximal end and attached to the interlock sleeve for rotation with the interlock sleeve at its distal end, wherein after said energy generating source is armed and the locking member has been moved into the unlocked position the energy generating source can be fired.

15. An injection device having a safety mechanism, wherein said injection device has a housing which includes a fluid chamber at least partially disposed therein, and an energy generating source, said safety mechanism comprising:

a triggering member disposed within the housing and operatively associated with the energy generating source so that movement of the triggering member activates the energy source to expel a fluid from the fluid chamber;

a locking member disposed on the exterior of the housing and operatively associated with the triggering member, said locking member being movable between a locked position and an unlocked position; and an interlock sleeve rotationally coupled with the locking member and having an aperture therein for receiving a lug, said interlock sleeve biased distally by a second biasing member, wherein:

movement of the triggering member is prevented when the locking member is in the locked position;

movement of the triggering member is possible when the locking member is in the unlocked position;

the housing and triggering member each have an aperture disposed thereon; and the locking member has a protruding lug which projects inwardly through the housing aperture and extends into the triggering member aperture, said lug being moveable within each of said apertures.

16. The safety mechanism of claim 15, wherein the second biasing member is a spring; the interlock sleeve has disposed thereon one or more raised surfaces; and the housing, at its distal end, includes a plurality of teeth so that the second biasing member biases the raised surface(s) of the interlock sleeve into engagement with the teeth to prevent rotational movement of the interlock sleeve.

17. The safety mechanism of claim 16 further comprising a disposable nozzle which defines the fluid chamber therein, said nozzle operatively associated with the interlock sleeve such that when the nozzle is removed from the housing, the interlock sleeve is biased by the second biasing member into rotational locking engagement with the housing and when the nozzle is installed in an operative position, the nozzle moves the interlock sleeve proximally out of engagement with the housing.

18. The safety mechanism of claim 17, wherein the second biasing member is a helical spring for biasing the interlock sleeve longitudinally into locking relationship, said spring being compressed when the nozzle is installed so that the raised surface(s) on the interlock sleeve is moved out of locking engagement with the teeth disposed on the housing.

19. The safety mechanism of claim 17 which further comprises an arming device including a tube and a cap which is removably and circumferentially disposed about the housing of the injector, wherein said tube is configured and dimensioned for receiving a distal end of the housing, and said cap is configured and dimensioned for receiving a proximal end of the energy generating source, wherein when the nozzle is removed from the injector after the energy generating source has been fired, the tube is attached to the housing and the cap is rotated to arm the energy generating source.

20. The safety mechanism of claim 19, wherein the tube further comprises an inwardly protruding portion located at the distal end of the tube for engaging the distal end of the housing, said inwardly protruding portion being configured and dimensioned for receiving the distal end of the housing after the nozzle has been removed therefrom, wherein as said inwardly protruding portion is attached to said housing, a proximal end of said inwardly protruding portion displaces the interlock sleeve proximally out of locking engagement with the housing.

21. The safety mechanism of claim 17, wherein said proximal end of the inwardly protruding portion has disposed thereon a plurality of ramps and steps; and a distal end of the interlock sleeve has disposed thereon a plurality of ramps and steps configured and dimensioned for coupling with said proximal end of the inwardly protruding portion, wherein when the tube engages the distal end of the housing, the ramps interact to push the interlock sleeve out of locking engagement with the housing and, after the injector has been armed by rotating the cap, as the tube is removed from the distal end of the housing, the steps couple to rotate the interlock sleeve to position the locking member in the locked position.

* * * * *

UNITED STATES PATENT AND TRADEMARK OFFICE
CERTIFICATE OF CORRECTION

PATENT NO.   :   5,865,795

DATED   :   February 2, 1999

INVENTORS   :   David SCHIFF et al.

It is certified that error appears in the above-identified patent and that said Letters Patent is hereby corrected as shown below:

Column 13, line 18: after "associated with the housing", insert --;-- and then on a new line and insert --wherein the housing and triggering member each have an aperture disposed thereon and the locking member has a protruding lug which projects inwardly through the housing aperture and extends into the triggering member aperture, said lug being moveable within each of said aperture--.

Signed and Sealed this

Twenty-first Day of September, 1999

*Attest:*

Q. TODD DICKINSON

*Attesting Officer*   *Acting Commissioner of Patents and Trademarks*